(12) United States Patent
Hygelund

(10) Patent No.: US 12,232,707 B2
(45) Date of Patent: Feb. 25, 2025

(54) ENDOSCOPE THERMAL REFLECTOR

(71) Applicant: ARTHREX, INC., Naples, FL (US)

(72) Inventor: John Hygelund, Santa Barbara, CA (US)

(73) Assignee: ARTHREX, INC., Naples, FL (US)

( * ) Notice: Subject to any disclaimer, the term of this patent is extended or adjusted under 35 U.S.C. 154(b) by 174 days.

(21) Appl. No.: 17/158,852

(22) Filed: Jan. 26, 2021

(65) Prior Publication Data

US 2022/0233062 A1 Jul. 28, 2022

(51) Int. Cl.
*A61B 1/06* (2006.01)
*A61B 1/00* (2006.01)
*A61B 1/07* (2006.01)

(52) U.S. Cl.
CPC ........ *A61B 1/0661* (2013.01); *A61B 1/00126* (2013.01); *A61B 1/07* (2013.01)

(58) Field of Classification Search
CPC ..... A61B 1/0661; A61B 1/00126; A61B 1/07; A61B 1/00165; A61B 1/00117; A61B 1/0017; A61B 1/00167
See application file for complete search history.

(56) References Cited

U.S. PATENT DOCUMENTS

| | | | |
|---|---|---|---|
| 4,953,937 A * | 9/1990 | Kikuchi | G02B 27/09 385/33 |
| 5,718,663 A * | 2/1998 | Wulfsberg | A61B 1/00096 600/176 |
| 5,966,210 A * | 10/1999 | Rosow | A61B 1/00165 356/213 |
| 6,124,883 A * | 9/2000 | Suzuki | A61B 1/00165 348/71 |
| 6,503,196 B1 * | 1/2003 | Kehr | A61B 1/00135 600/176 |
| 8,480,566 B2 | 7/2013 | Farr | |
| 8,672,838 B2 * | 3/2014 | McDowall | A61B 1/051 600/176 |
| 9,271,637 B2 | 3/2016 | Farr | |
| 9,459,415 B2 | 10/2016 | Feingold et al. | |
| 10,524,862 B2 | 1/2020 | Van der Weide et al. | |
| 10,667,672 B2 | 6/2020 | Juergens | |
| 10,786,205 B2 * | 9/2020 | Hellstrom | A61B 1/00135 |
| 2001/0008485 A1 * | 7/2001 | Fuji | H01J 61/34 362/345 |

(Continued)

FOREIGN PATENT DOCUMENTS

| FR | 2954087 | 2/2012 |
|---|---|---|
| JP | 6438062 | 12/2018 |

(Continued)

OTHER PUBLICATIONS

The International Search Report and The Written Opinion, dated Apr. 19, 2022, pp. 1-14.

*Primary Examiner* — Anh Tuan T Nguyen
*Assistant Examiner* — Shankar Raj Ghimire
(74) *Attorney, Agent, or Firm* — KARISH & BJORGUM, PC

(57) ABSTRACT

An endoscope system for use with a light guide having an endoscope; and a reflector configured for placement between the endoscope and the light guide. The reflector has a translucent portion for transmitting light from the light guide and a reflective portion for reflecting light from the light guide back into the light guide.

26 Claims, 4 Drawing Sheets

(56) References Cited

U.S. PATENT DOCUMENTS

| | | | |
|---|---|---|---|
| 2004/0064018 A1* | 4/2004 | Dunki-Jacobs | A61B 1/07 600/178 |
| 2005/0020926 A1* | 1/2005 | Wiklof | G02B 27/0994 348/E9.011 |
| 2005/0096642 A1* | 5/2005 | Appling | A61B 18/24 606/15 |
| 2005/0279354 A1* | 12/2005 | Deutsch | A61M 16/0463 128/200.24 |
| 2006/0069314 A1* | 3/2006 | Farr | A61B 1/0653 600/179 |
| 2006/0198418 A1* | 9/2006 | Hama | G02B 6/262 372/6 |
| 2007/0093690 A1* | 4/2007 | Hopkins | G02B 6/4298 600/180 |
| 2008/0089089 A1* | 4/2008 | Hama | F21V 9/38 362/574 |
| 2008/0221388 A1* | 9/2008 | Seibel | A61B 1/00172 600/109 |
| 2009/0221991 A1* | 9/2009 | Lieponis | A61B 1/00105 604/540 |
| 2011/0282155 A1* | 11/2011 | Kase | A61B 1/0615 600/176 |
| 2012/0053420 A1* | 3/2012 | Kasamatsu | A61B 1/0638 600/182 |
| 2012/0099112 A1* | 4/2012 | Alphonse | G01B 9/02044 385/12 |
| 2013/0345517 A1* | 12/2013 | Morimoto | A61B 1/0638 600/178 |
| 2014/0042467 A1* | 2/2014 | Livesay | F21V 7/24 257/88 |
| 2014/0092227 A1* | 4/2014 | Kanamori | A61B 1/07 348/68 |
| 2014/0107496 A1* | 4/2014 | Hellstrom | A61B 5/0086 600/478 |
| 2016/0128557 A1 | 5/2016 | Papac et al. | |
| 2016/0374545 A1* | 12/2016 | Obara | A61B 1/00009 600/109 |
| 2017/0100023 A1 | 4/2017 | Vayser | |
| 2017/0188802 A1* | 7/2017 | Lawrence | A61B 1/0607 |
| 2019/0008376 A1* | 1/2019 | Wortelboer | A61B 5/6852 |
| 2019/0033506 A1* | 1/2019 | Weber | A61B 1/00167 |
| 2021/0149101 A1* | 5/2021 | Swanson | G02B 23/26 |
| 2022/0061638 A1* | 3/2022 | Hinding | A61B 1/00117 |
| 2022/0233062 A1* | 7/2022 | Hygelund | A61B 1/00117 |
| 2023/0040005 A1* | 2/2023 | Charles | A61F 9/00736 |
| 2023/0392996 A1* | 12/2023 | Namiki | G01K 3/12 |

FOREIGN PATENT DOCUMENTS

| | | |
|---|---|---|
| WO | 2019049997 | 3/2019 |
| WO | 2019077693 | 4/2019 |

* cited by examiner

ENDOSCOPE THERMAL REFLECTOR

BACKGROUND

The present disclosure relates to devices used in endoscopic surgery and, more particularly, to thermal reflectors for use in endoscopes.

Light guides transfer light from a light source to an endoscope. Light guides are typically sized to work with the largest endoscopes. When light guides are used with smaller endoscopes there are unavoidable losses at the connection point, because the amount of light that can be concentrated into the smaller endoscope fiber bundle area is limited by geometric properties of light. This leads to heat buildup at the connection point which may lead to discomfort for a user and a dangerous surgical situation.

Therefore it would be desirable to prevent unnecessary light and heat from reaching an endoscope.

SUMMARY

The present disclosure relates to an endoscope system with a reflector for reflecting some light back into a light guide to reduce heat in an endoscope. In an implementation, an endoscope system for use with a light guide has an endoscope; and a reflector configured for placement between the endoscope and the light guide. The reflector has a translucent portion for transmitting light from the light guide and a reflective portion for reflecting light from the light guide back into the light guide.

The endoscope may have a light post and the reflector may be configured for placement between the light guide and the light post. The reflector may have a flat reflective portion, an inwardly angled reflective portion or a curved reflective portion. The reflector may have an annular shape. A light source may be coupled to the light guide.

In another implementation, an endoscope system has an endoscope with a body; and a light post coupled to the body, the light guide having a first active area of light transmission. The endoscope system also has a light guide, the light guide having a second active area of light transmission and a connector for connecting the light guide to the light post. The endoscope system also has a reflector configured for placement between the light guide and the light post. The reflector has a translucent portion for transmitting light from the light guide and a reflective portion for reflecting light from the light guide back into the light guide. The first active area has a smaller diameter than the second active area.

The translucent portion may have a diameter corresponding to a diameter of the first active area. The reflector may have an outer diameter that is smaller than a diameter of the connector. Optionally, the translucent portion has a diameter corresponding to a diameter of the first active area; and the reflector is configured to fit inside of the connector. The reflector further may have a flat reflective portion, an inwardly angled reflective portion or a curved reflective portion. The reflector may have an annular shape with an inner diameter corresponding to a diameter of the first active area. A light source may be coupled to the light guide.

In another implementation there is disclosed a reflector for use in an endoscope system with an endoscope and a light guide, the reflector comprising a translucent portion for transmitting light from the light guide; and a reflective portion for reflecting light from the light guide back into the light guide. The reflector may be configured for placement between the endoscope and the light guide. The reflective portion may be flat, inwardly angled, or curved. Additionally, the reflector may have an annular shape.

These and other features are described below.

BRIEF DESCRIPTION OF THE DRAWINGS

The features, aspects and advantages of the present invention will become better understood with regard to the following description, appended claims and accompanying figures wherein:

DETAILED DESCRIPTION

In the following description of the preferred implementations, reference is made to the accompanying drawings which show by way of illustration specific implementations in which the invention may be practiced. Wherever possible, the same reference numbers will be used throughout the drawings to refer to the same or like parts. It is to be understood that other implementations may be utilized and structural and functional changes may be made without departing from the scope of this disclosure.

Figure 1:
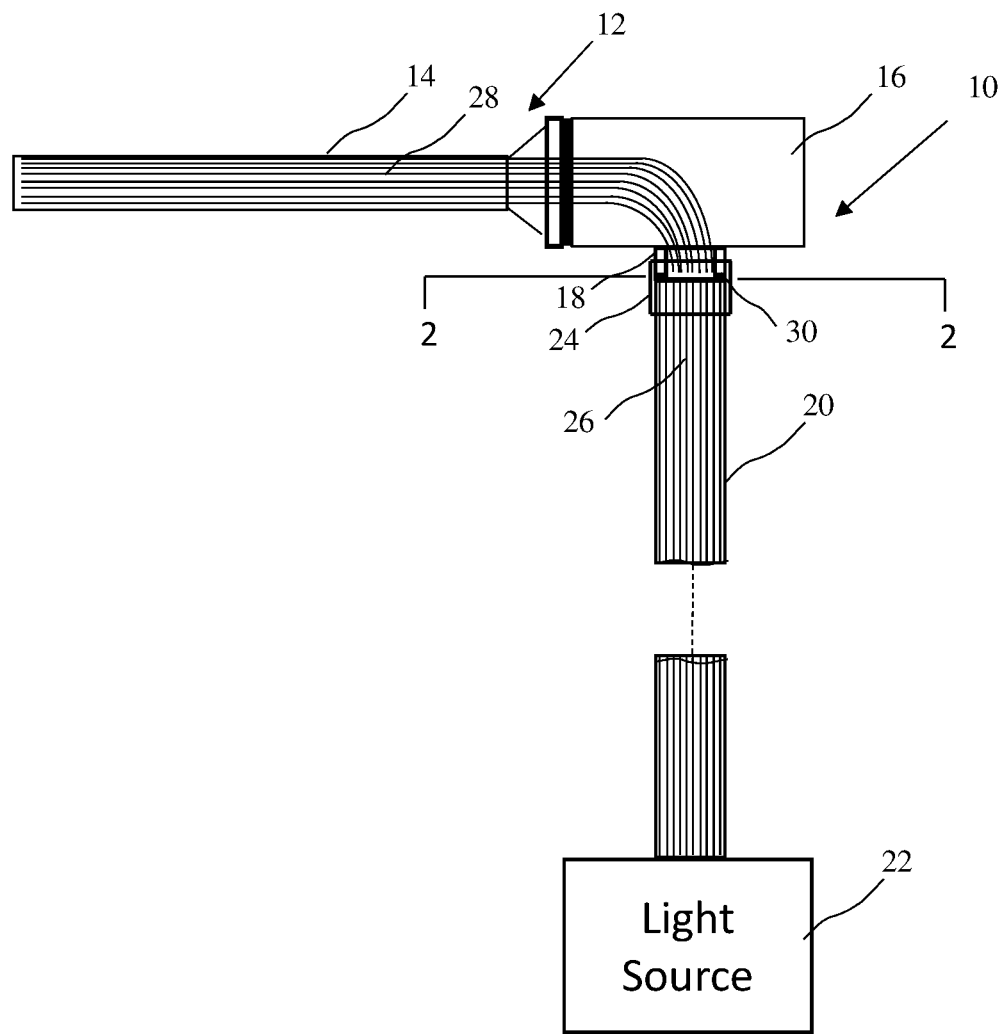
FIG. 1 is a schematic diagram of a endoscope system according to an implementation.
Figure 2:
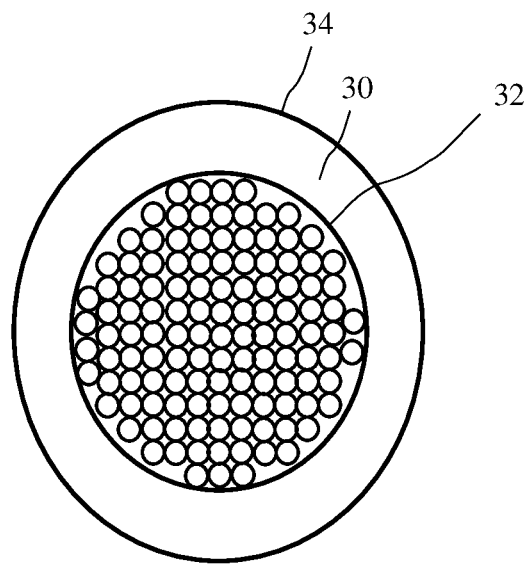
FIG. 2 is a cross sectional view of a light post taken along line 2-2 of FIG. 1.
Figure 3:
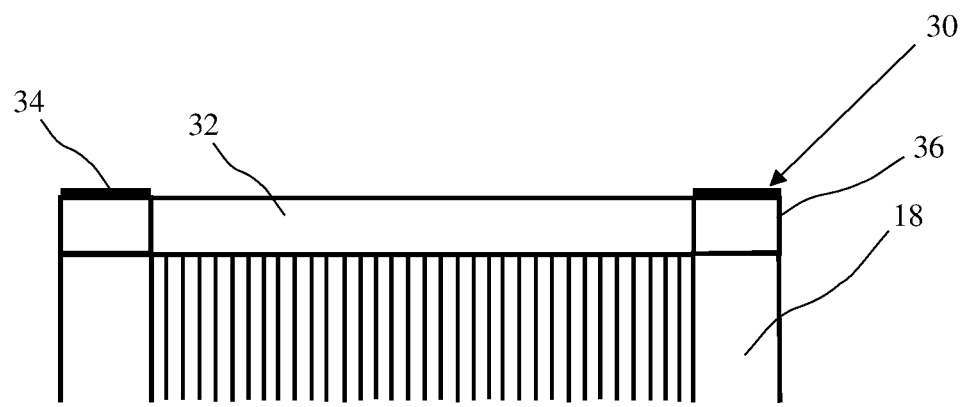
FIG. 3 is a cross sectional elevation view of a light post with a thermal reflector according to an implementation.

With reference to FIGS. 1 to 3, an endoscope system 10 according to an implementation has an endoscope 12 with a shaft 14 and a body 16. The body 16 has a light post 18 for receiving light from a light guide 20 coupled to a light source 22. As used herein, the term "light post" is intended to include, for example and without limitation, standard and non-standard interfaces for accepting light from a light source. The light guide 20 may be removably connected to the light post 18 using a connector 24, for example, a threaded connector, a snap fit connector or a friction (push on) fit connector.

The light source 22 may produce visible light. The light source 22 may also produce non-visible wavelengths of radiation, such as, for example, near infra-red radiation or ultraviolet radiation, that may be transmitted with or without visible light. As used herein, the term "light" includes visible light as well as non-visible wavelengths of radiation. The light source 22 may have, for example, a xenon lamp or a light emitting diode (LED) lamp.

As used herein, the term "light guide" includes any waveguide or cable for transmitting light from a light source to an endoscope. For example and without limitation, the light guide 20 may be a flexible cable with fiber optics 26 for transmitting light from the light source 22. Light is transferred from the light guide fiber optics 26 into endoscope fiber optics 28. Representative fiber optics 26, 28 are shown in FIG. 1. Although fiber optics are used to illustrate certain implementations, this disclosure is intended to encompass other means of light transfer through the light guide 18 and through the endoscope 12.

The light guide 20 may have an active diameter of light transmission (for example, the diameter of a fiber optic bundle) greater than an endoscope 12 active diameter of light transmission. For example, some light guides have an active diameter greater than about 4.5 mm and some endoscopes have an active diameter less than about 4 mm. Other endoscopes may have an active diameter of less than about 3 mm or less than about 2 mm; with some endoscopes having an active diameter as small as 0.5 mm. When a light guide has a greater active diameter than the endoscope then some light is not transferred from the light guide fiber optics into the endoscope fiber optics, but rather is transferred onto the light source post 18. In addition, this tapering from light guide to endoscope excites higher angles and broadens the field of view of the exiting illumination. This constraint prevents optimization for efficiency.

As shown in FIG. 3, a thermal reflector 30 according to an implementation is configured for positioning proximal to an interface between the light guide fiber optics 26 and the endoscope fiber optics 28. The thermal reflector 30 is configured with a translucent portion 32 to allow light to pass through an area corresponding to the endoscope active diameter and a reflective portion 34 to reflect light directed to areas outside of the endoscope active diameter. As illustrated below, the reflective portion 34 may be flat (perpendicular to the direction of light from the light guide 20), angled or curved.

The thermal reflector 30 may be made of glass, clear plastic, or metal. The reflective portion 34 may be manufactured by polishing metal or depositing a reflective coating of metal, such as aluminum or silver onto a portion of the glass or plastic. Thin film deposition may be used to create the reflective coating. The thermal reflector 30 has an outer diameter 36 that is slightly smaller than an inner diameter of a light guide connector 24 so that the thermal reflector may sit within the connector when the connector is attached to the light post. The thermal reflector 30 may have an outer diameter 36 of from about 3 mm to about 20 mm and more preferably from about 8 mm to about 13 mm. The thermal reflector may have a height of from about 5 to about 15 mm and more preferably from about 7.5 mm to about 12.5 mm. In an implementation, the thermal reflector 30 is specific to the endoscope fiber optics 28 and reflects light from about 10% to about 95% of the light guide fiber optics 26. Depending on a diameter of the endoscope fiber optics 28, the reflective portion 34 may have an inner diameter less than about 4 mm, and possibly less than about 2.3 mm, and possibly less than about 0.9 mm.

Figure 4:
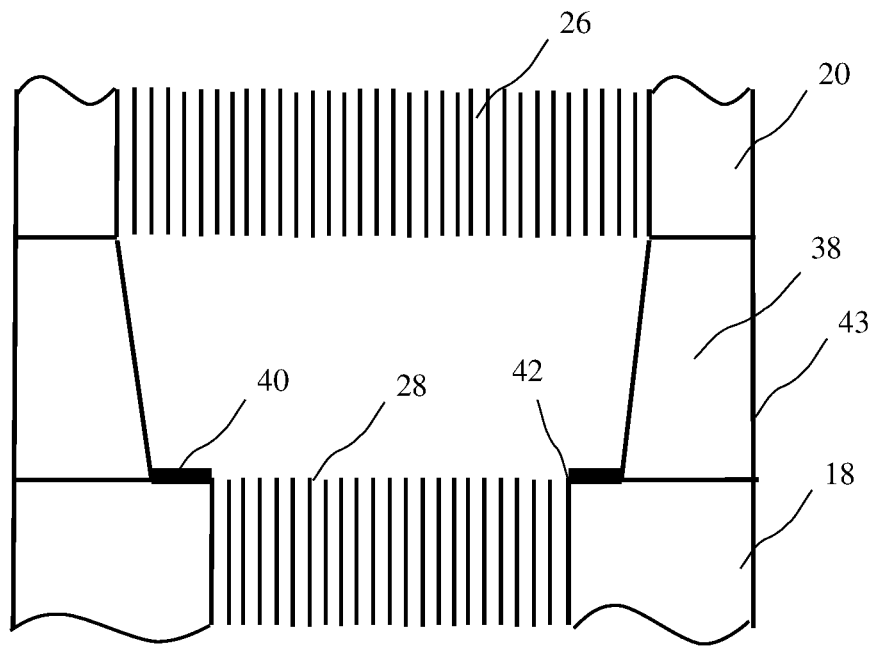
FIG. 4 is a cross sectional elevation view of a light post with a thermal reflector according to an implementation.

In an additional implementation, as shown in FIG. 4, a thermal reflector 38 has a reflective portion 40 that is annularly shaped with a flat reflective surface. The thermal reflector 38 has an inner diameter 42 that is slightly larger than the endoscope fiber optic active diameter. The thermal reflector 38 has an outer diameter 43 that is slightly smaller than an inner diameter of a light guide connector 24 so that the thermal reflector may sit within the connector when the connector is attached to the light post. The reflective portion 34 may be formed of, for example, aluminum or silver, or a thin film.

Figure 5:
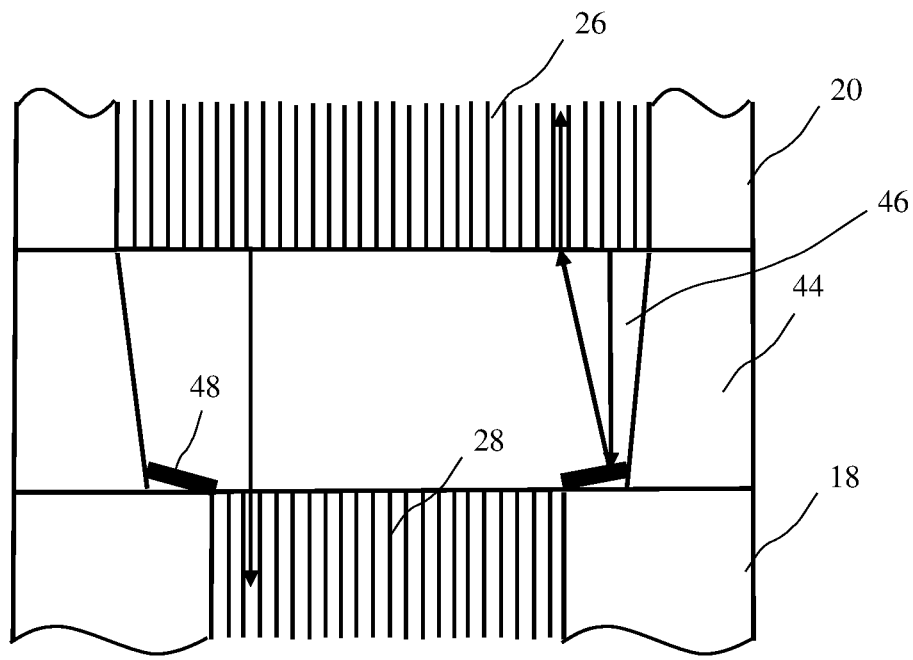
FIG. 5 is a cross sectional elevation view of a light post with a thermal reflector according to an implementation.

In an additional implementation, as shown in FIG. 5, a thermal reflector 44 has a translucent portion 46 and an inwardly angled reflective surface 48. The reflective surface 48 may be at an angle less than about 10 degrees relative to an axis perpendicular to the direction of light from the light guide 20 so that light is reflected back into the light guide. The thermal reflector 44 may also be formed as an annular shape with the translucent portion 46 being an opening.

Figure 6:
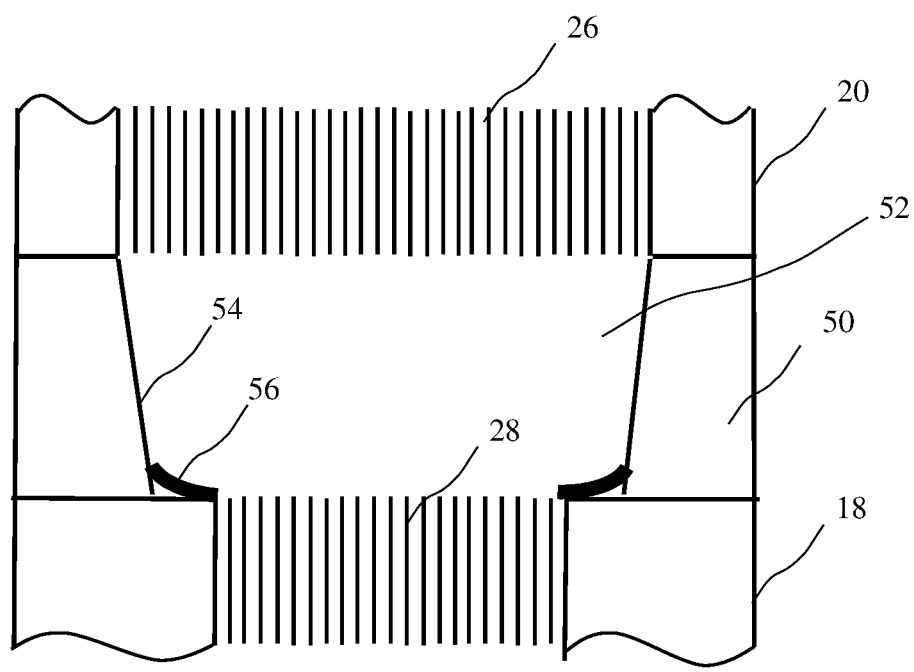
FIG. 6 is a cross sectional elevation view of a light post with a thermal reflector according to an implementation.

In an additional implementation, as shown in FIG. 6, a thermal reflector 50 is formed as an annular shape with a central opening 52 (translucent portion) formed by an inner wall 54 and a curved reflective surface 56. The reflective surface 56 may have a consistent radius of curvature or more complex conic or freeform shape. The reflective surface may have a radius of curvature less than about 10 mm. The thermal reflector 50 may also be formed as an annular shape with the translucent portion 52 being an opening.

Optionally, the inner wall 54 conically tapers from a larger diameter, such as proximal to the light guide, to a smaller diameter, such as proximal to the light post. The inner wall 54 may also be reflective. The inner wall 54 may be configured to totally internally reflect light so that a surface treatment of the inner wall 54 is not necessary. The thermal reflector may also be formed as a cylindrical shape with a solid translucent portion (not shown).

Additionally, a converter (not shown) may be interposed between the light post 18 and the light guide connector 24 to allow for linkage of light posts and light guides having different diameters. A thermal reflector 34 may be placed in the connection between the light post and the converter. The thermal reflector 34 may also be placed in the connection between the converter and the light guide connector 24.

The thermal reflector is advantageous in reducing heat caused by light that is not transmitted into an endoscope and allows for greater combinations of endoscopes and light sources. Additionally, the thermal reflector may be used in existing endoscope light systems without substantial modifications. Additionally, the thermal reflector is a relatively low cost solutions.

There is disclosed in the above description and the drawings, an endoscope thermal reflector that fully and effectively overcomes the disadvantages associated with the prior art. However, it will be apparent that variations and modifications of the disclosed implementations may be made without departing from the principles of the invention. The presentation of the implementations herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. An endoscope system for use with a light guide comprising:
   an endoscope; and
   a reflector configured for placement between the endoscope and the light guide; and
   wherein the reflector has a translucent portion for transmitting light from the light guide and an annular shaped reflective portion for reflecting light from the light guide back into the light guide; and wherein at least some of the reflective portion between edges of the light guide is at a non-zero angle relative to an axis perpendicular to a direction of light from the light guide.

2. The endoscope system of claim 1 wherein the endoscope further comprises a light post and the reflector is configured for placement between the light post and the light guide.

3. The endoscope system of claim 1 wherein the reflector further comprises a flat reflective portion.

4. The endoscope system of claim 3 wherein the reflector further comprises an annular shape.

5. The endoscope system of claim 1 wherein the reflector further comprises an inwardly angled reflective portion.

6. The endoscope system of claim 5 wherein the reflector further comprises an annular shape.

7. The endoscope system of claim 1 wherein the reflector further comprises a curved reflective portion.

8. The endoscope system of claim 7 wherein the reflector further comprises an annular shape.

9. The endoscope system of claim 1 further comprising the light guide; and a light source coupled to the light guide.

10. An endoscope system comprising:
  an endoscope further comprising:
    a body;
    a light post coupled to the body, the light post having a first active area of light transmission;
  a light guide, the light guide having a second active area of light transmission; and
  a connector for connecting the light guide to the light post; and
  a reflector configured for placement between the light guide and the light post;
  wherein the reflector has a translucent portion for transmitting light from the light guide and an annular shaped reflective portion for reflecting light from the light guide back into the light guide; wherein at least some of the reflective portion between edges of the light guide is at a non-zero angle relative to an axis perpendicular to a direction of light from the light guide; and
  wherein the first active area has a smaller diameter than a diameter of the second active area.

11. The endoscope system of claim 10 wherein the translucent portion has a diameter corresponding to the diameter of the first active area.

12. The endoscope system of claim 10 wherein the connector has a diameter and wherein the reflector has an outer diameter that is smaller than the connector diameter.

13. The endoscope system of claim 10 wherein the translucent portion has a diameter corresponding to the diameter of the first active area; and wherein the reflector is configured to fit inside of the connector.

14. The endoscope system of claim 10 wherein the reflector further comprises a flat reflective portion.

15. The endoscope system of claim 14 wherein the reflector further comprises an annular shape with an inner diameter corresponding to the diameter of the first active area.

16. The endoscope system of claim 10 wherein the reflector further comprises an inwardly angled reflective portion.

17. The endoscope system of claim 16 wherein the reflector further comprises an annular shape with an inner diameter corresponding to the diameter of the first active area.

18. The endoscope system of claim 10 wherein the reflector further comprises a curved reflective portion.

19. The endoscope system of claim 18 wherein the reflector further comprises an annular shape with an inner diameter corresponding to the diameter of the first active area.

20. The endoscope system of claim 10 further comprising a light source coupled to the light guide.

21. A reflector for use in an endoscope system with an endoscope and a light guide, the reflector comprising:
  a translucent portion for transmitting light from the light guide; and an annular shaped reflective portion for reflecting light from the light guide back into the light guide;
  wherein at least some of the reflective portion between edges of the light guide is at a non-zero angle relative to an axis perpendicular to a direction of light from the light guide; and
  wherein the reflector is configured for placement between the endoscope and the light guide.

22. The reflector of claim 21 wherein the reflective portion is flat.

23. The reflector of claim 21 wherein the reflective portion is inwardly angled.

24. The reflector of claim 21 wherein the reflective portion is curved.

25. The reflector of claim 21 wherein the reflector further comprises an annular shape.

26. An endoscope system for use with a light guide comprising:
  an endoscope; and
  a reflector configured for placement between the endoscope and the light guide; and
  wherein the reflector has a translucent portion for transmitting light from the light guide and an annular shaped reflective portion for reflecting light from the light guide back into the light guide; and wherein a substantial amount of the reflective portion is at a non-zero angle relative to an axis perpendicular to a direction of light from the light guide.

* * * * *